US00PP33963P2

(12) United States Plant Patent
Cousins

(10) Patent No.: US PP33,963 P2
(45) Date of Patent: Feb. 22, 2022

(54) GRAPEVINE PLANT NAMED 'EJG TWO'

(50) Latin Name: ***Vitis interspecific* hybrid**
Varietal Denomination: EJG Two

(71) Applicant: E&J Gallo Winery, Modesto, CA (US)

(72) Inventor: Peter Samuel Melugin Cousins, Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 17/351,072

(22) Filed: Jun. 17, 2021

(51) Int. Cl.
*A01H 6/88* (2018.01)
*A01H 5/08* (2018.01)

(52) U.S. Cl.
USPC ..... Plt./207

(58) Field of Classification Search
USPC ..... Plt./207
See application file for complete search history.

*Primary Examiner* — Annette H Para
(74) *Attorney, Agent, or Firm* — Goodwin Procter LLP

(57) ABSTRACT

A new and distinct variety of grapevine plant named 'EJG Two' characterized by its production of grapes with a distinct and pleasant sweet herbal and mint flavor. The grapes are suitable for making white wine with sweet herbal and mint flavors and aromas. 'EJG Two' vines are fertile with spur pruning.

9 Drawing Sheets

Latin name of the genus and species of the plant claimed: The plant claimed relates to a new and distinct variety of *Vitis* interspecific hybrid.

Variety denomination: The plant claimed shall be known as 'EJG Two'.

STATEMENT REGARDING FEDERALLY SPONSORED RESEARCH OR DEVELOPMENT

The present invention is not a subject of any federally sponsored research or development.

BACKGROUND OF THE INVENTION

The new and distinct grapevine described and claimed herein originated from a wine grape breeding program. Hand pollination of the flowers of Symphony grape (U.S. Plant Pat. No. 5,013) as the seed parent variety with pollen of a non-patented pollen parent variety was performed in May 2013, and the resulting seeds were germinated in a greenhouse. The seedling vines were planted in a vineyard near Ripperdan, Madera County, Calif. in April 2014. The present variety of grapevine was selected as a single plant in August 2016 based on fruit yield, flavor, and composition, and was first asexually propagated by hardwood cuttings at Arroyo Grande, San Luis Obispo County, Calif. in February 2017. The resulting propagules were planted in the vineyard in May 2017 near Ripperdan, Madera County, Calif., as a replicated planting of ten vines. The resulting vines were found to be true to type, showing attributes of the original vine when observed in fruit for at least two seasons. Wine was made from fruit harvested from these ten vines and the wine was evaluated through chemical and sensory testing.

BRIEF SUMMARY OF THE INVENTION

The following description relates to the 'EJG Two' grapevine when grown under normal horticultural practices near Ripperdan, Madera County, Calif. Some of the characteristics of the grapevine may vary depending upon changes in crop load and/or change of location of cultivation.

The 'EJG Two' grapevine is characterized by producing medium-large dense clusters of medium-large grapes (alternatively referred to herein as "fruit" or "berries") with a distinct and pleasant sweet herbal and mint flavor. 'EJG Two' grapes have green-yellow skin, which is commonly recognized in viticulture and enology as "white." The grapes ripens for winemaking each year in August. 'EJG Two' flowers are perfect and self-fertile with functional stamens, viable pollen, and a functional pistil. 'EJG Two' grapes have normal development of seeds. 'EJG Two' is fertile with spur pruning. 'EJG Two' grapes are suitable for white wine production and the wine is distinguished by positive and enjoyable sweet herbal, mint, and eucalyptus aromas and flavors, which demonstrate the usefulness of 'EJG Two'.

'EJG Two' differs from its pollen parent by producing berries with normal seed development, while its pollen parent produces grapes with stenospermocarpic seed development, which is an incomplete form of seed development in grapevine that results in effectively seedless berries that do not develop hard seed coats. Microsatellite (e.g., simple sequence repeat) markers were used to develop a DNA fingerprint of 'EJG Two', and comparison of the 'EJG Two' DNA fingerprint to an extensive, non-public database of grapevine variety DNA fingerprints showed that the 'EJG Two' DNA fingerprint was different from all the other DNA fingerprints. This observation is consistent with the origin of a 'EJG Two' as a distinct grapevine that arose from a seed that was the result of pollination between varieties.

The commercially grown wine grape varieties that are the most similar to 'EJG Two' are Muscat blanc (also known as Muscat Canelli; non-patented) and Symphony (U.S. Plant Pat. No. 5,013), which is the seed parent of 'EJG Two'. 'EJG Two' differs from Muscat blanc in several important ways. For example, 'EJG Two' has larger clusters than Muscat blanc, and the berries of 'EJG Two' at harvest are greener in color than the berries of Muscat blanc. At harvest, Muscat blanc berries are more yellow than 'EJG Two' berries. 'EJG Two' also differs from its seed parent, Symphony, in several important ways. For example, 'EJG Two' produces grapes with a strong sweet herbal and mint flavor, while Symphony produces muscat-flavored grapes that lack the flavor of sweet herbs and mint. 'EJG Two' ripens for winemaking in August, substantially before Symphony, which is ordinarily harvested in September. Both Symphony and Muscat blanc berries are distinctly muscat flavored, while 'EJG Two' does not produce distinctly muscat flavored grapes.

BRIEF DESCRIPTION OF THE DRAWINGS

The accompanying photographs illustrate 'EJG Two' in full color. The colors are as nearly true as is reasonably possible in a color representation of this type. For reference, many of the photographs include the following: a 24-color card sold by CAMERATRAX, a code number (13028028) that was used for testing 'EJG Two', and gridlines in which each square is 1 cm×1 cm. The grapevines and portions thereof shown in the photographs were grown in the vicinity of Ripperdan, Madera County, Calif. The photographs were obtained during the year 2020 when the grapevines were about three (3) years old.

DETAILED BOTANICAL DESCRIPTION

Figure 1:
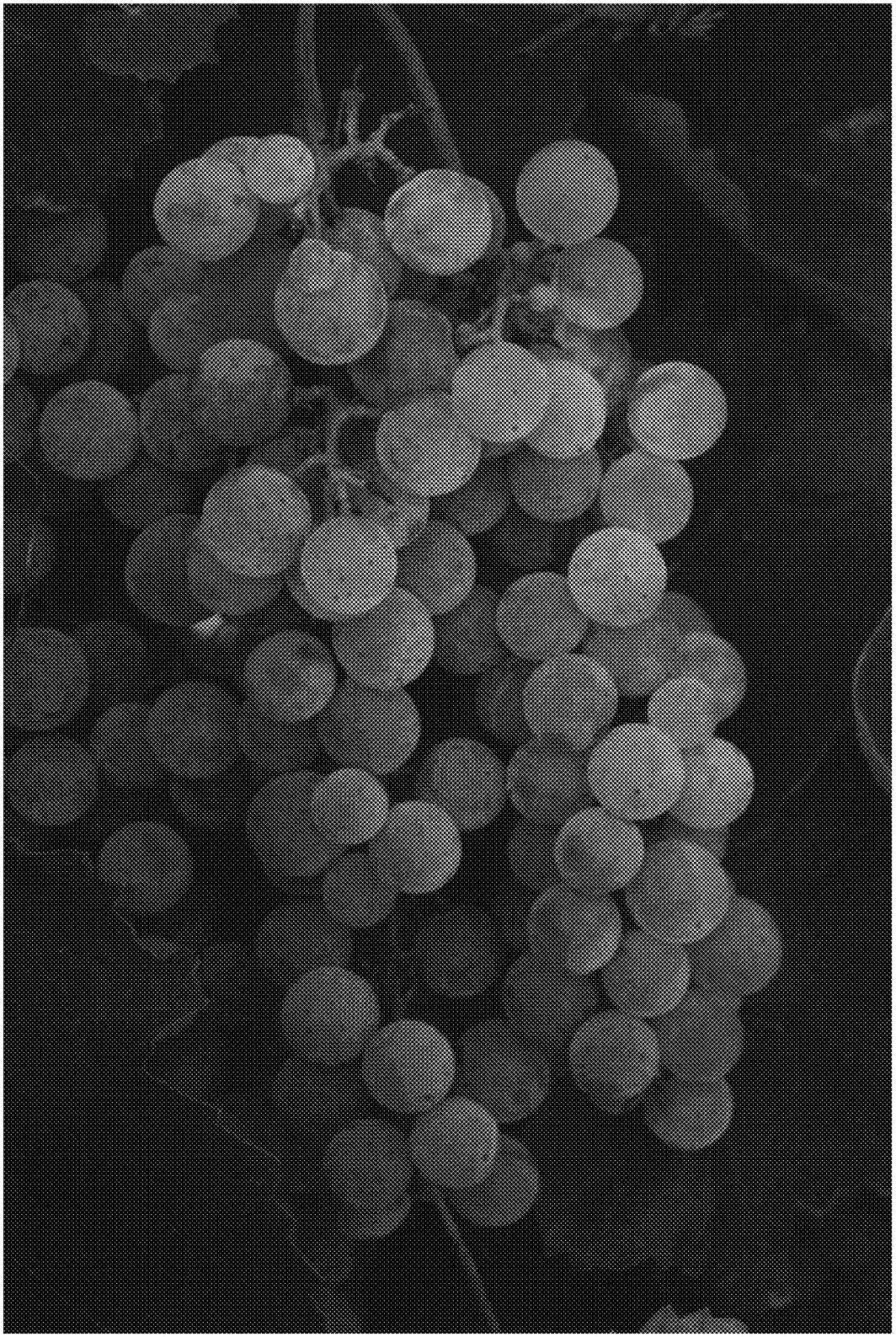
FIG. 1 includes a photograph of a grape cluster on 'EJG Two' during August.
Figure 2:
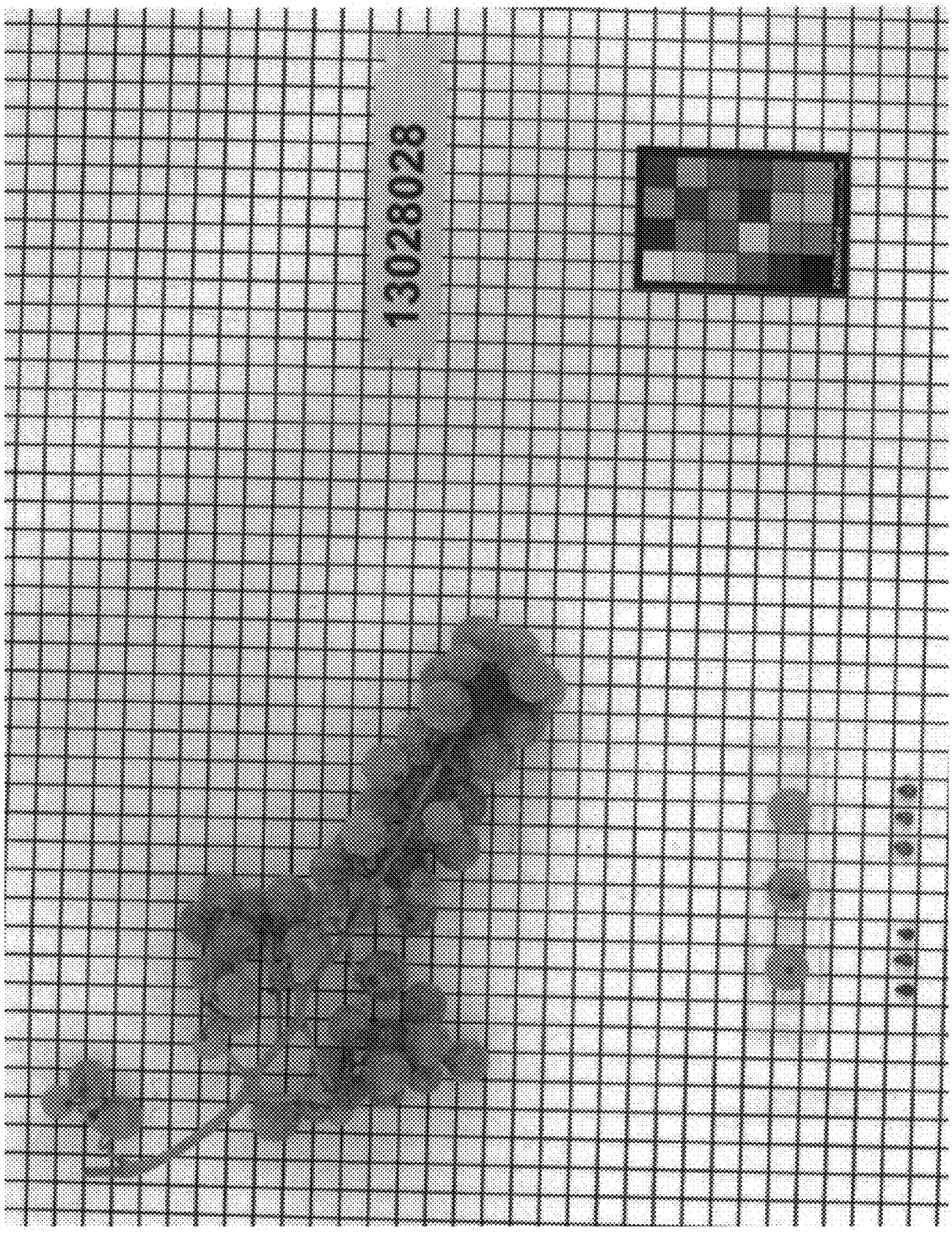
FIG. 2 includes a photograph of a grape cluster, three grapes, and six seeds during September. A grape in the middle of the three grapes has been cut in half.
Figure 3:
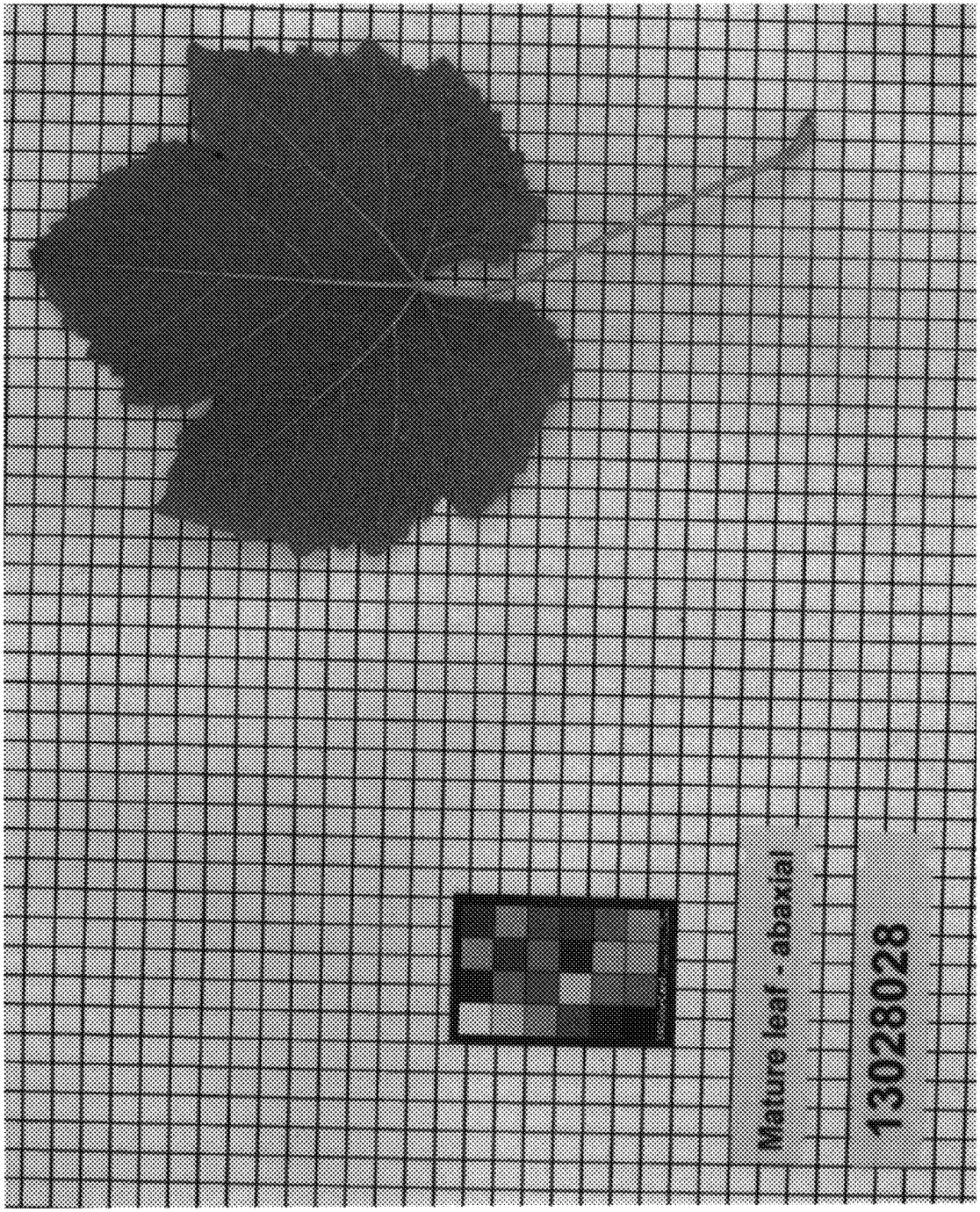
FIG. 3 includes a photograph of an abaxial surface of a mature leaf during July.
Figure 4:
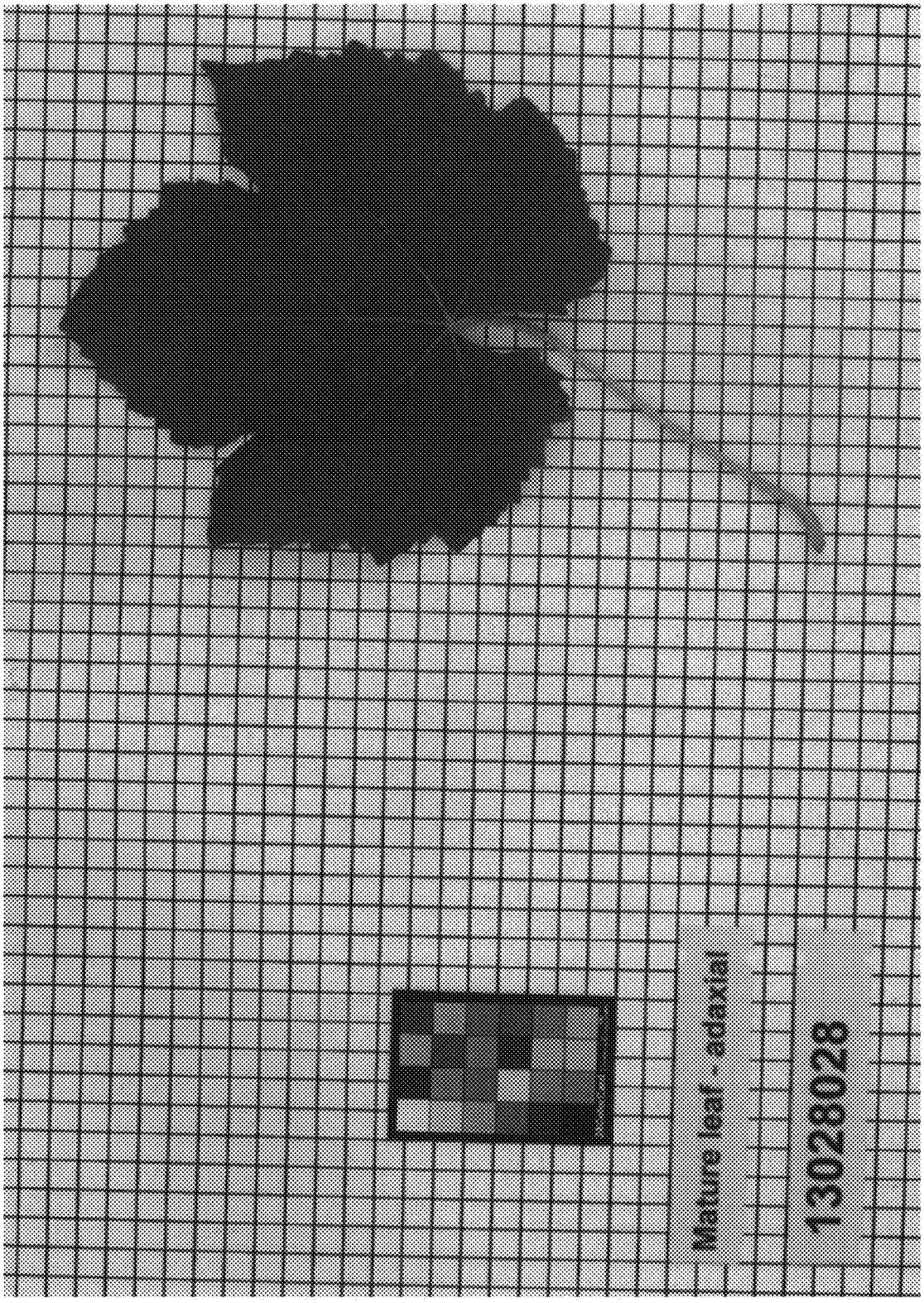
FIG. 4 includes a photograph of an adaxial surface of a mature leaf during July.
Figure 5:
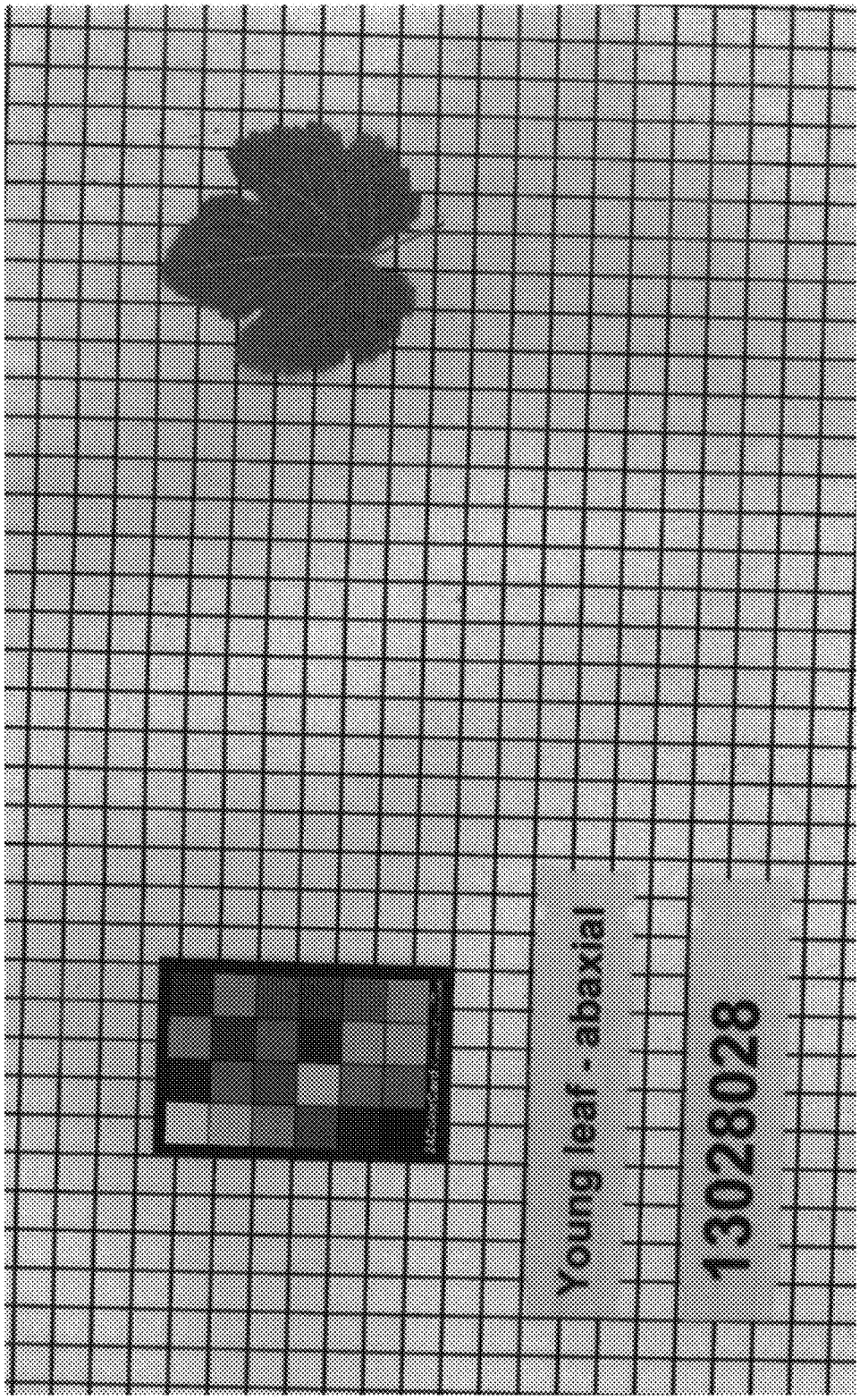
FIG. 5 includes a photograph of an abaxial surface of a young leaf during July.
Figure 6:
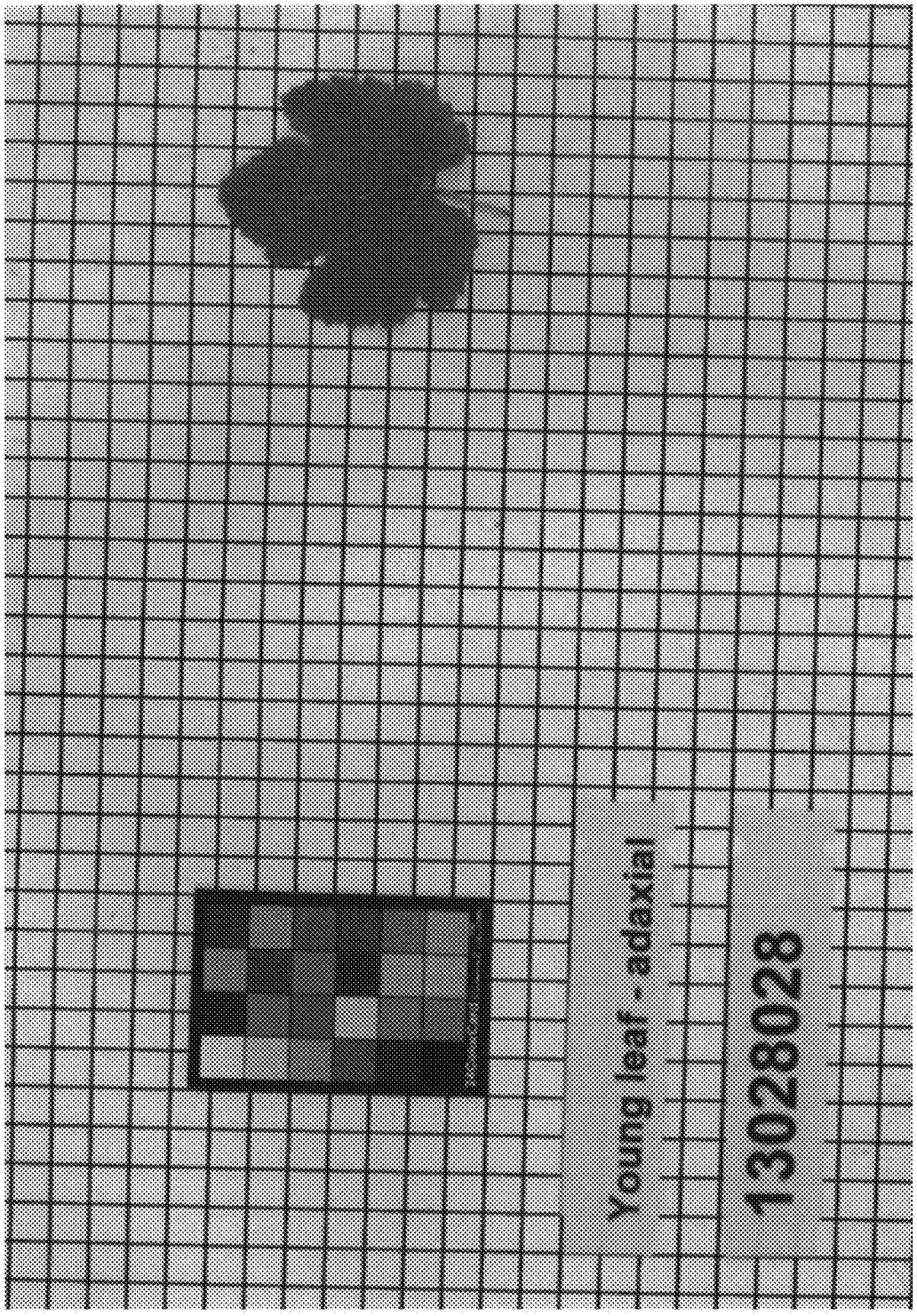
FIG. 6 includes a photograph of an adaxial surface of a young leaf during July.
Figure 7:
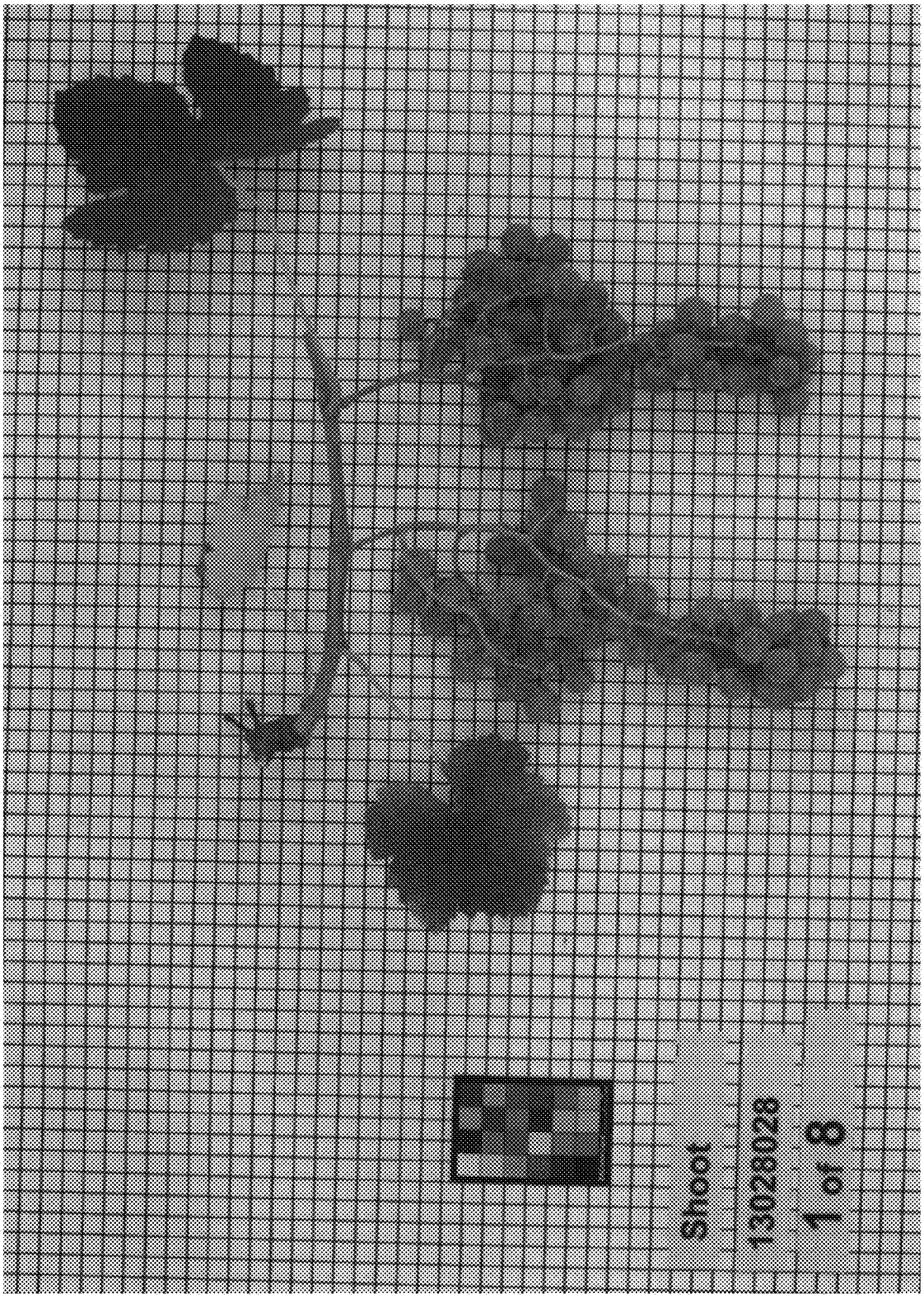
FIG. 7 includes a photograph of a shoot base during July.
Figure 8:
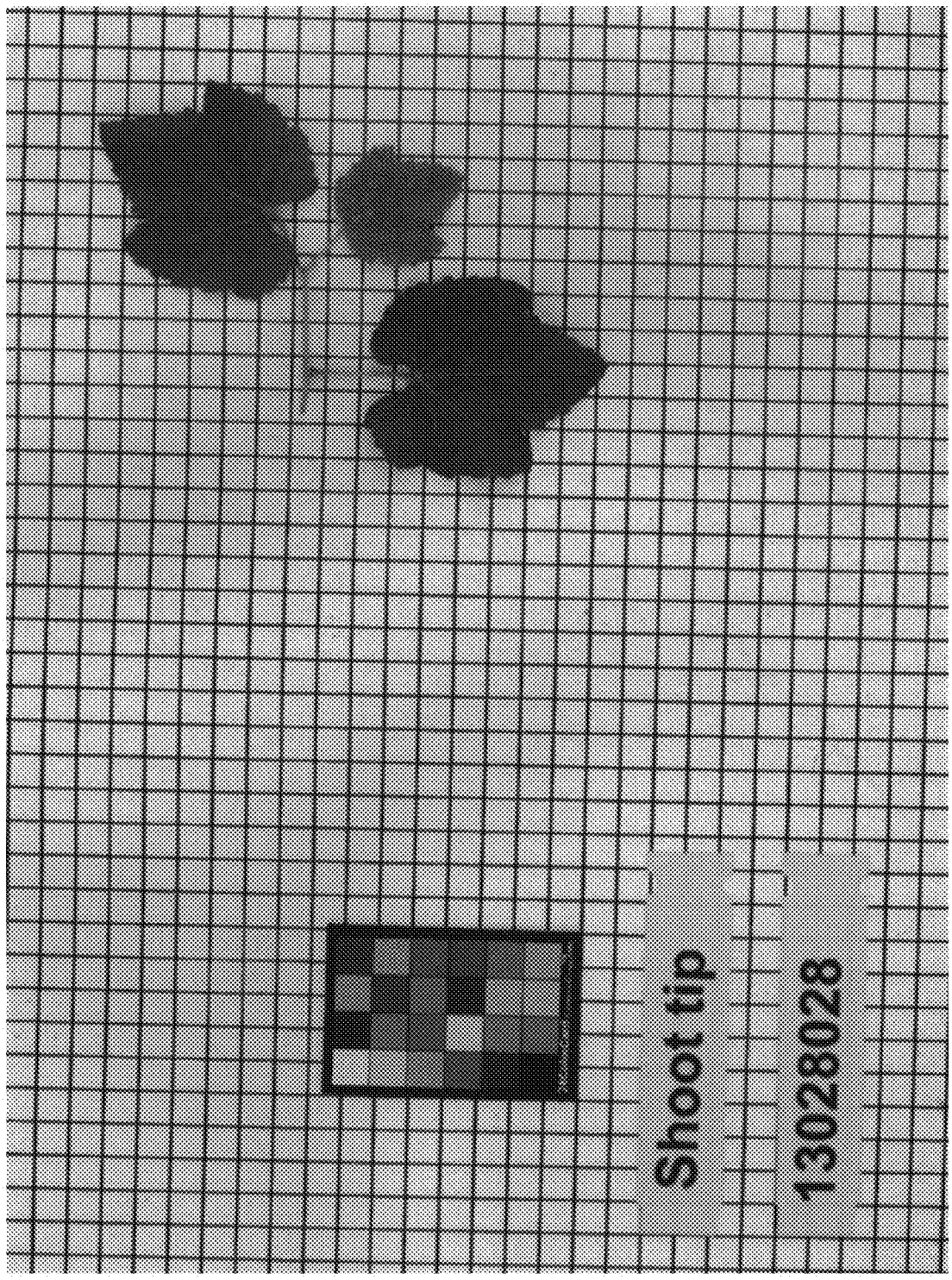
FIG. 8 includes a photograph of a shoot tip during July.
Figure 9:
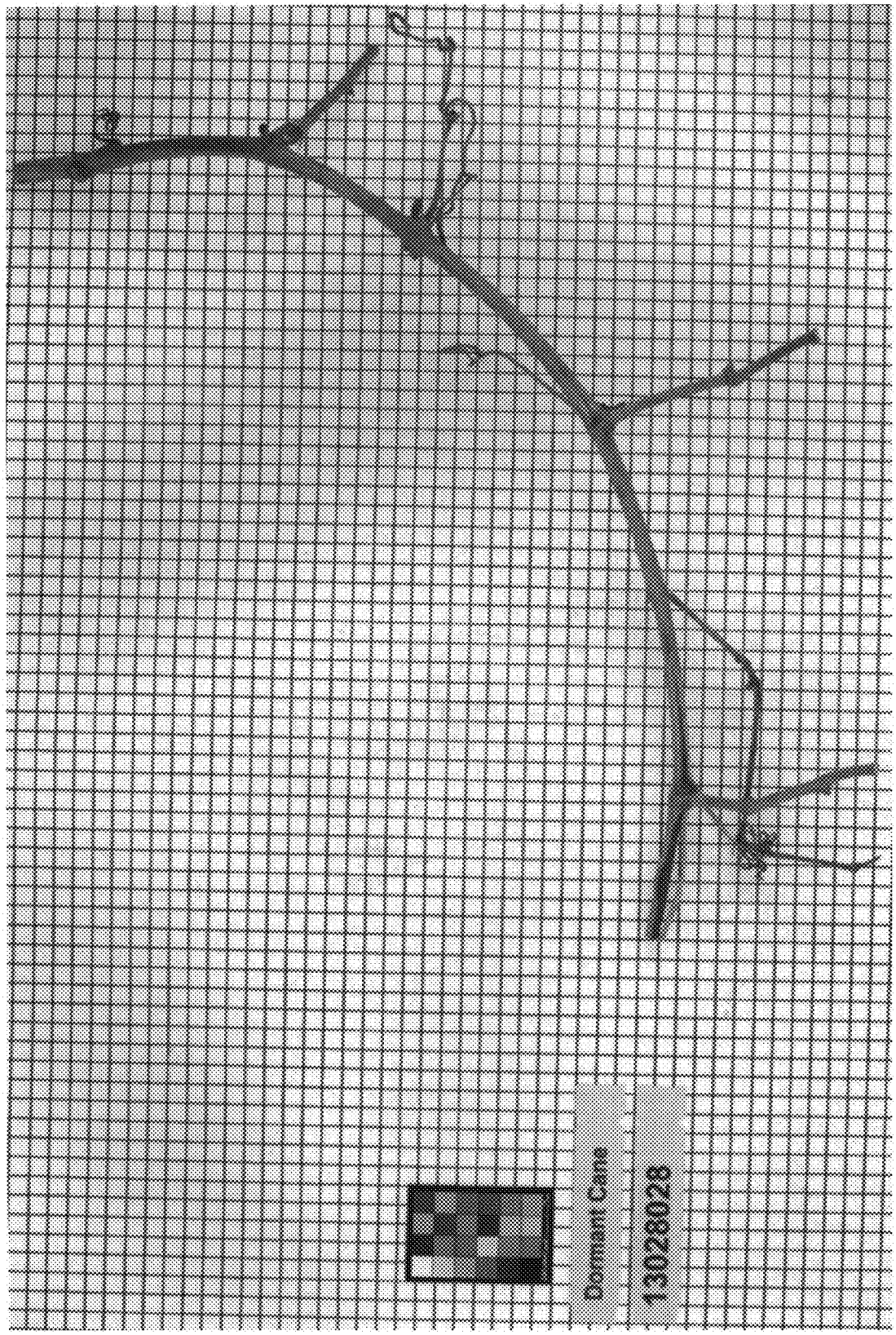
FIG. 9 includes a photograph of a dormant cane during December.

The following detailed description sets forth the distinctive characteristics of 'EJG Two'. Colors refer to the designations of the Munsell Book of Color Glossy Collection, Part No. 40115B, Serial No. 55635311119. The descriptions pertain to grapevines grown in the vicinity of Ripperdan, Madera County, Calif. that were observed during 2020 and other years, and the descriptions are believed to apply to plants of the variety grown under similar conditions elsewhere. The vines from which the observations were made were grown on their own roots (not grafted).

Buds:

*Bud break date.*—Apr. 2, 2020.

Cluster:

*Berries per cluster.*—70.
*Cluster density.*—Dense.
*Cluster length.*—182.1 mm.
*Cluster width.*—120.3 mm.
*Clusters per shoot.*—2.
*Peduncle length.*—46.2 mm.
*Rachis color.*—5GY 5/6; Green-Yellow.
*Weight.*—187 g.

Flower:

*First bloom date.*—May 5, 2020.
*Full bloom date.*—May 18, 2020.
*Flower diameter.*—2.0 mm.
*Flower length.*—3 mm.
*Flowers per cluster.*—709.
*Node location of first inflorescence.*—4.
*Type.*—Self-fertile hermaphrodite (perfect) with erect stamens.

Fruit:

*Attachment.*—Easy to detach.
*Berry flesh color.*—Colorless.
*Berry skin color.*—5GY 5/4; Green-Yellow.
*Berry diameter at equator.*—18.4 mm.
*Berry length.*—17.8 mm.
*Berry diameter at base.*—3.4 mm.
*Berry weight.*—2.5 g.
*Brush length.*—6.2 mm.
*Firmness.*—Soft.
*Harvest date, day of year.*—223.
*Juiciness.*—Very juicy.
*Pulp texture.*—Soft.
*Skin thickness.*—Thin.

Juice:

*Color.*—Colorless.

Leaves:

*Arrangement of mature leaves (phyllotaxy).*—Alternate.
*Color of mature leaves, base abaxial.*—7.5GY 4/4; Green-Yellow.
*Color of mature leaves, base adaxial.*—7.5GY 2/4; Green-Yellow.
*Color of mature leaves, midpoint abaxial.*—7.5GY 4/4; Green-Yellow.
*Color of mature leaves, midpoint adaxial.*—7.5GY 2/4; Green-Yellow.
*Color of mature leaves, terminal abaxial.*—7.5GY 4/4; Green-Yellow.
*Color of mature leaves, terminal adaxial.*—7.5GY 2/4; Green-Yellow.
*Color of veins on mature leaves, abaxial surface.*—2.5GY 8/2; Green-Yellow.
*Color of veins on mature leaves, adaxial surface.*—7.5R 3/4; Red.
*Color of young leaves, base abaxial.*—5P 8/2; Purple.
*Color of young leaves, base adaxial.*—2.5GY 5/6; Green-Yellow.
*Color of young leaves, midpoint abaxial.*—5P 8/2; Purple.
*Color of young leaves, midpoint adaxial.*—2.5GY 5/6; Green-Yellow.
*Color of young leaves, terminal abaxial.*—5P 8/2; Purple.
*Color of young leaves, terminal adaxial.*—2.5GY 5/6; Green-Yellow.
*Length of mature leaves.*—157 mm.
*Thickness of mature leaves.*—0.4 mm.
*Width of mature leaves.*—150.1 mm.
*Leaf pubescence on young leaves, abaxial surface.*—Minimal.
*Leaf pubescence on young leaves, adaxial surface.*—Minimal.
*Margin of mature leaves.*—Serrate with large and small teeth.
*Marginal teeth height.*—3.6 mm.

*Marginal teeth width.*—6 mm.
*Number of lobes on mature leaves.*—5.
*Petiole sinus of mature leaves*.—Lobes half open.
*Pubescence on mature leaves, abaxial side*.—Present.
*Pubescence on mature leaves, adaxial side*.—Absent.
*Shape of mature leaves*.—Pentagonal.
*Surface texture of mature leaves, abaxial side*.—Smooth.
*Surface texture of mature leaves, adaxial side*.—Smooth.
*Vein color of young leaves, abaxial side.*—10Y 8/2; Yellow.
*Vein color of young leaves, adaxial side.*—10Y 8/2; Yellow.
*Venation of mature leaves*.—Usual.

Petioles:
*Color of mature petioles.*—7.5R 3/6; Red.
*Color of young petioles.*—2.5GY 6/6; Green-Yellow.
*Length of mature petioles.*—133 mm.
*Thickness at base of mature petioles.*—4.8 mm.
*Pubescence on mature petioles*.—Abundant.
*Shape of mature petioles*.—Round.

Seed:
*Color.*—5R 4/2; Red.
*Length.*—6.4 mm.
*Number per berry.*—1.
*Seed development*.—Complete, producing typical hard brown seeds.
*Seeds present/absent*.—Present.
*Shape*.—Pyriform.
*Weight.*—0.04 g.
*Width.*—4.3 mm.

Shoots (current-season canes):
*Color of shoots.*—5GY 5/6; Green-Yellow.
*Length of internode above cluster.*—70.6 mm.
*Node color.*—5GY 5/6; Green-Yellow.
*Shoot attitude*.—Semi erect.
*Width at node bearing cluster.*—11.8 mm.

Tendrils:
*Color of mature tendril.*—10Y 6/8; Yellow.
*Length.*—205.1 mm.
*Thickness at base.*—2.7 mm.
*Node location of first tendril.*—8.
*Phyllotaxy* (*pattern*).—Intermittent.
*Ramification*.—Branched.
*Texture*.—Smooth.

Trunk:
*Color.*—10YR 6/2; Yellow-Red.
*Diameter at* 30 *cm above soil level.*—184.6 mm.
*Shape*.—Round.

Vine:
*Density of foliage*.—Dense.
*Growth vigor*.—High.
*Productivity*.—High.
*Size*.—Large.

What is claimed is:

1. A new and distinct variety of grapevine plant named 'EJG Two', substantially as illustrated and described herein.

* * * * *